US010632150B1

(12) United States Patent
Thomas et al.

(10) Patent No.: US 10,632,150 B1
(45) Date of Patent: Apr. 28, 2020

(54) POTASSIUM PHOSPHATES COMPOSITION FOR INJECTION

(71) Applicant: CMP Development LLC, Farmville, NC (US)

(72) Inventors: H. Greg Thomas, Flowery Branch, GA (US); Richard LeVasseur, Flowery Branch, GA (US); Jeffrey S. Kiel, Flowery Branch, GA (US); Anthony Reid Pipho, Winterville, NC (US)

(73) Assignee: CMP Development LLC, Farmville, NC (US)

( * ) Notice: Subject to any disclaimer, the term of this patent is extended or adjusted under 35 U.S.C. 154(b) by 0 days.

(21) Appl. No.: 16/389,181

(22) Filed: Apr. 19, 2019

Related U.S. Application Data

(60) Provisional application No. 62/748,008, filed on Oct. 19, 2018.

(51) Int. Cl.
*A61K 33/42* (2006.01)
*A61K 9/00* (2006.01)

(52) U.S. Cl.
CPC ............ *A61K 33/42* (2013.01); *A61K 9/0019* (2013.01)

(58) Field of Classification Search
CPC .............................. A61K 33/42; A61K 9/0019
See application file for complete search history.

(56) References Cited

U.S. PATENT DOCUMENTS

| 5,736,207 A | 4/1998 | Walther et al. |
| 2009/0029399 A1* | 1/2009 | O'Brien .................. C12Q 1/48 435/15 |
| 2015/0297800 A1 | 10/2015 | Weikart et al. |
| 2018/0221243 A1 | 8/2018 | Weikart et al. |

FOREIGN PATENT DOCUMENTS

| CN | 106265499 A | 1/2017 |

OTHER PUBLICATIONS

CN 106265499A, English translation of tables in para [0034], [0037-0038], 2017, p. 1 (Year: 2017).*
Aluminum in Large and Small Volume Parenterals Used in Total Parenteral Nutrition, Federal Register, Jan. 26, 2000, vol. 65, No. 17, 4103-4111.
Mullin et al., Growth Kinetics of Ammonium- and Potassium-Dihydrogen Phosphate Crystals, J. Appl. Chem. (1967) 17(5): 151-156.
Poole et al., Aluminum in Pediatric Parenteral Nutrition Products: Measured Versus Labeled Content, J. Pediatr. Pharmacol. Ther. (2011) 16(2): 92-97.
Poole et al., Aluminum Exposure from Pediatric Parenteral Nutrition: Meeting the New FDA Regulation, J. Parenter. Enteral. Nutr. (2008) 32(3): 242-246.
Ogawa et al., Effects of Phosphate Buffer in Parenteral Drugs on Particle Formation from Glass Vials, Chem. Pharm. Bull. (2013) 61(5): 539-545.
Ogawa et al., Aluminum elution and precipitation in glass vials: effect of pH and buffer species, Drug Dev. Ind. Pharm. (2015)41(2): 315-321.
Merck Index (1976), Monograph No. 7446 at 7447; 3 pages.
Hospira, Potassium Phosphates Injection, USP; EN-0554 (Oct. 2004); 3 pages.
Package Insert, Fresenius Kabi; Potassium Phosphates Injection, USP (Feb. 2015); 4 pages.
PerformRx (Sep. 2017) Drug Information Update; 72 pages.
Fresenius Kabi; Phosphate Injection Availability, May 29, 2013; 6 pages.
American Regent; Nov. 2005 Label, Potassium Phosphates; 1 page.
Luitpold Pharmaceuticals, Inc.—American Regent Product Safety Data Sheet; Mar. 22, 2010; 7 pages.
American Regent Initiates Nationwide Voluntary Recall of Potassium Phosphates Injection; Feb. 3, 2011; 5 pages.
The United States Pharmacopeial Convention (Aug. 1, 2012); Particulate Matter in Injections (788) 5157-5160; 4 pages.
International Search Report and Written Opinion for PCT/US2019/028355 dated Aug. 1, 2019 (16 pages).

* cited by examiner

*Primary Examiner* — Sarah Pihonak
(74) *Attorney, Agent, or Firm* — Merchant & Gould P.C.; Daniel R. Evans

(57) ABSTRACT

Disclosed herein is a sterile composition for injection comprised of potassium phosphates having no visible particulate. Also disclosed herein is a manufacturing process for the sterile composition and its use.

21 Claims, No Drawings

POTASSIUM PHOSPHATES COMPOSITION FOR INJECTION

RELATED APPLICATION

The present application claims priority to U.S. Provisional Patent Application No. 62/748,008, filed on Oct. 19, 2018.

FIELD OF THE INVENTION

Disclosed herein is a sterile composition for injection comprised of potassium phosphates having no visible particulate. Also disclosed herein is a manufacturing process for the sterile composition and its use.

BACKGROUND

Potassium Phosphates Injection, USP 3 mM P/mL (3 millimoles phosphate/mL), hereafter "PPI," is a sterile, nonpyrogenic, concentrated solution containing a mixture of potassium monobasic phosphate ("KMP") and potassium dibasic phosphate ("KDP") in water for injection contained in a glass vial. The solution is administered after dilution by the intravenous route as an electrolyte replenisher. Each milliliter of PPI contains 224 mg of KMP and 236 mg of KDP. The specified storage conditions for PPI depend on the manufacturer. For instance, one manufacturer states that PPI should be stored between 15° C. to 30° C., while another manufacturer states that PPI should be stored between 20° C. to 25° C. Package inserts related to PPI recommend visually inspecting the products for particulate matter. The formation of insoluble particles is one of the most critical incidents for pharmaceutical companies, which results in recalls of drug products from the market. See, e.g., Ogawa (2013) and Ogawa (2015). Indeed, manufacturers in the past have initiated voluntary recalls of PPI products due to the presence of visible particles. Not surprisingly, product recalls lead to product shortages and create problems for attending physicians in need of PPI.

Another potential problem with marketed PPI products is the aluminum content, especially after long-time storage. A high aluminum content conflicts with recent recommendations to minimize the amount of aluminum in parenteral products. For instance, Poole (2011) states that certain patient populations having renal insufficiency can experience problems associated with aluminum toxicity. Poole (2011) also states that recorded manifestations of aluminum toxicity include fracturing osteomalacia and reduced bone mineralization, neurological dysfunction and dialysis encephalopathy, microcytic hypochromic anemia, and cholestasis. In an effort to minimize the possibility that a patient having renal insufficiency will be exposed to unacceptable levels of aluminum in parenteral products, the U.S. Food and Drug Administration ("FDA") has promulgated regulations in an effort to minimize the amount of aluminum in parenteral products. See, e.g., FDA Regulations (2000) and Poole (2008). In that regard, Poole (2011) recommends a maximum daily aluminum dose of 4 to 5 mcg/kg/day in patients having impaired renal function to avoid aluminum accumulation and toxicity. Poole (2011) evaluated the labeled and measured aluminum content in PPI products. In view of the products marked at that time with labeled contents that range from 51,000 mcg/L to 62,500 mcg/L, Poole (2011) concluded that the aluminum levels were high—more recently developed products have labeled aluminum levels of 31,000 mcg/L.

In view of the foregoing, it is clear that PPI products are problematic. In response to these problems, the inventors sought to solve the visible particulate problem, and thus, sought to solve the problems associated with product availability. Further, the inventors sought to solve the aluminum content problem associated with glass vials containing the potassium phosphates compositions described herein.

SUMMARY

After a detailed investigation, it was determined that the aforementioned problems are solved by a sterile composition for injection, comprising: (a) about 175 mg/mL potassium monobasic phosphate; (b) about 300 mg/mL of potassium dibasic phosphate; and (c) a sufficient amount of a water vehicle; wherein the total amount of phosphate is about 3 mmol/mL. It also was determined that the aforementioned problems are solved by a sterile composition for injection, comprising: (a) about 136 mg/mL potassium monobasic phosphate and (b) a sufficient amount of a water vehicle; wherein the total amount of phosphate is about 1 mmol/mL.

DETAILED DESCRIPTION

A first embodiment is directed to a sterile composition for injection, comprising: (a) about 175 mg/mL potassium monobasic phosphate; (b) about 300 mg/mL of potassium dibasic phosphate; and (c) a sufficient amount of a water vehicle; wherein the total amount of phosphate is about 3 mmol/mL.

A second embodiment is directed to a sterile composition for injection, consisting of: (a) about 175 mg/mL potassium monobasic phosphate; (b) about 300 mg/mL of potassium dibasic phosphate; and (c) a sufficient amount of a water vehicle; wherein the total amount of phosphate is about 3 mmol/mL.

In a first aspect of the first or second embodiment, the composition has an amount of potassium that is about 185 mg/mL.

In a second aspect of the first or second embodiment, the composition has a pH of about 6.5 to about 7.5 or about 6.8 to about 7.0.

In a third aspect of the first or second embodiment, the composition has a pH of about 6.8 to about 7.0.

In a fourth aspect of the first or second embodiment, the composition has a pH of about 6.9.

In a fifth aspect of the first or second embodiment, the composition has no visible particles after storage at 4-8° C. for 3-months, 6-months, 12-months, 18-months, 24-months, 30-months, 36-months, 42-months, 48-months, 54-months, 60-months, 66-months, 72-months, 78-months, 84-months, 90-months, or 96-months.

In a sixth aspect of the first or second embodiment, the composition has no visible particles after storage at about 25° C. and 60% relative humidity for 3-months, 6-months, 12-months, 18-months, 24-months, or longer.

A seventh aspect of the first or second embodiment is directed to a vial (e.g., glass or plastic) comprising the composition of the first or second embodiment. A particularly advantageous feature of the seventh aspect is that the composition has no visible particles after storage at 4-8° C. for 3-months, 6-months, 12-months, 18-months, 24-months, 30-months, 36-months, 42-months, 48-months, 54-months, 60-months, 66-months, 72-months, 78-months, 84-months, 90-months, or 96-months.

An eighth aspect of the first or second embodiment is directed to a glass vial comprising the composition of the first or second embodiment having an aluminum content of not more than about 15 ppm after storage at 4-8° C. for 3-months, 6-months, 12-months, 18-months, 24-months, 36-months, or longer (e.g., 48-months).

A ninth aspect of the first or second embodiment is directed to a glass vial comprising the composition of the first or second embodiment having an aluminum content of not more than about 10 ppm after storage at 4-8° C. for 3-months, 6-months, 12-months, 18-months, or longer (e.g., 24-months). An aluminum content of not more than about 10 ppm after storage at 4-8° C. for 18-months or longer (e.g., 24-months) is particularly surprising when the composition is stored in a glass vial.

A tenth aspect of the first or second embodiment is directed to a plastic vial comprising the composition of the first or second embodiment having an aluminum content of not more than about 5 ppm, about 4 ppm, about 3 ppm, about 2 ppm, or about 1 ppm after storage at 4-8° C. for 3-months, 6-months, 12-months, 18-months, 24-months, 36-months, or longer (e.g., 48-months). The plastic vial optionally comprises a coating comprised of SiO2.

An eleventh aspect of the first or second embodiment is directed to a plastic vial comprising the composition of the first or second embodiment having an aluminum content of not more than about 5 ppm, about 4 ppm, about 3 ppm, about 2 ppm, or about 1 ppm after storage at room temperature for 3-months, 6-months, 12-months, 18-months, 24-months, 36-months, or longer (e.g., 48-months). The plastic vial optionally comprises a coating comprised of SiO2.

A twelfth aspect of the first or second embodiment is directed to a vial (e.g., glass or plastic) comprising the composition of the first or second embodiment, wherein a volume of the sterile composition is about 5 mL, about 7.5 mL about 15 mL, or about 50 mL.

A thirteenth aspect of the first or second embodiment is directed to a vial (e.g., glass or plastic) comprising the composition of the first or second embodiment, wherein a volume of the sterile composition is about 15 mL to about 16 mL.

A fourteenth aspect of the first or second embodiment is directed to a method for treating hypophosphatemia in a patient in need thereof, which comprises: diluting the composition of the first or second embodiment with a pharmaceutically acceptable diluent to obtain a diluted composition and intravenously administering the diluted composition to the patient.

The pharmaceutically acceptable diluent includes, for example, sterile water for injection, dextrose (D5W), or other diluents that are compatible with the intended use for treating hypophosphatemia.

A fifteenth aspect of the first or second embodiment is directed to a method for treating hypophosphatemia in a patient in need thereof, which comprises: diluting the composition of the first or second embodiment with a pharmaceutically acceptable diluent to obtain a diluted composition and intravenously administering the diluted composition to the patient, wherein the patient exposure to aluminum is less than about 10 mcg/kg/day, less than about 7.5 mcg/kg/day, or less than about 5 mcg/kg/day.

A sixteenth aspect of the first or second embodiment is directed to a method for treating hypophosphatemia in a patient in need thereof, which comprises: diluting the composition of the first or second embodiment with a pharmaceutically acceptable diluent to obtain a diluted composition and intravenously administering the diluted composition to the patient, wherein the patient exposure to aluminum is less than about 5 mcg/kg/day.

A seventeenth aspect of the first or second embodiment is directed to a process for preparing the composition of the first or second embodiment, which comprises: (a) dissolving an amount of potassium dibasic phosphate in a vessel containing a first amount of water that represents about 25% of the total amount of water; (b) adding a second amount of water that represents about 60% of the total amount of water to the composition of step (a); (c) dissolving an amount of potassium monobasic phosphate in the composition of step (b); (d) adding a third amount of water to the composition of step (c) to provide about 175 mg/mL potassium monobasic phosphate and about 300 mg/mL of potassium dibasic phosphate; and (e) filtering the composition of step (d) through a membrane having a plurality of pores each with a pore diameter of about 0.2 μm.

The filter comprised of a membrane having a plurality of pores each with a pore diameter of about 0.2 μm comprises a membrane comprising a pharmaceutically acceptable polymer, for example, polyethersulfone or polyvinylidine difluoride.

An eighteenth aspect of the first or second embodiment is directed to a process for preparing the composition of the first or second embodiment, which comprises: (a) dissolving an amount of potassium dibasic phosphate in a vessel containing a first amount of water that represents about 25% of the total amount of water; (b) adding a second amount of water that represents about 60% of the total amount of water to the composition of step (a); (c) dissolving an amount of potassium monobasic phosphate in the composition of step (b); (d) adding a third amount of water to the composition of step (c) to provide about 175 mg/mL potassium monobasic phosphate and about 300 mg/mL of potassium dibasic phosphate; (e) filtering the composition of step (d) through a membrane having a plurality of pores each with a pore diameter of about 0.2 μm; (f) dispensing a volume of the composition of step (e) into a vial; (g) sealing the vial of step (f); and (h) heating the vial of step (g) at a temperature of about 121° C. for about 15 minutes to about 30 minutes.

A nineteenth aspect of the first or second embodiment is directed to a vial (e.g., glass or plastic) obtained by the process of the eighteenth aspect, which comprises: (a) about 175 mg/mL potassium monobasic phosphate; (b) about 300 mg/mL of potassium dibasic phosphate; (c) a sufficient amount of a water vehicle; wherein the total amount of phosphate is about 3 mmol/mL.

A twentieth aspect of the first or second embodiment is directed to a glass vial obtained by the process of the eighteenth aspect, which comprises: (a) about 175 mg/mL potassium monobasic phosphate; (b) about 300 mg/mL of potassium dibasic phosphate; (c) a sufficient amount of a water vehicle; wherein the total amount of phosphate is about 3 mmol/mL.

A twenty-first aspect of the first or second embodiment is directed to a plastic vial obtained by the process of the seventeenth aspect, which comprises: (a) about 175 mg/mL potassium monobasic phosphate; (b) about 300 mg/mL of potassium dibasic phosphate; (c) a sufficient amount of a water vehicle; wherein the total amount of phosphate is about 3 mmol/mL.

Suitable vials can be glass or plastic. Examples of glass vials include those manufactured by Schott or SiO2 Medical, including, for example, Schott Delamination Control (DC) Vial (e.g., Via Inject 20R DC Clear EBB Type 1), Schott Type I plus vials having a SiO2 coating (e.g., Schott One Plus (Type 1 glass vial with silicon dioxide coating 20R)). Examples of plastic vials include those manufactured by SiO2 Medical, including, for example, a medical grade cyclic olefin polymer (COP) with (e.g., SiO2Plas Vial (COP with SiO2 coating) 2R, 6R, 10R, or 20R) or without a SiO2 coating (e.g., COP Vial 2R, 6R, 10R, or 20R). See Weikart (2015) and Weikart (2018).

Suitable stoppers are manufactured by, for example, West Pharmaceuticals, and include, for example, STV 1242 4110/40/Grey B2-40 or 20 mm Serum NovaPure RP S10-F451 4432/50G (gray elastomer having FluroTec® barrier film). Suitable flip-off tops are manufactured by, for example, Datwyler Pharma Packaging, and include, for example, CLS Flip-Off Grey 20 mm SFC 20.0001 or 20F0 LQ TE (6-B) 3766 WHT (aluminum closure with white Flip top cap).

A twenty-second aspect of the first or second embodiment comprises diluting the sterile composition for injection by a factor of about three using an additional amount of a water vehicle; wherein the total amount of phosphate is about 1 mmol/mL.

A twenty-third aspect of the first or second embodiment relates to a sterile composition for injection, comprising (or consisting of): (a) about 58.3 mg/mL potassium monobasic phosphate; (b) about 100 mg/mL of potassium dibasic phosphate; and (c) a sufficient amount of a water vehicle; wherein the total amount of phosphate is about 1 mmol/mL.

A twenty-fourth aspect of the first or second embodiment relates to a vial comprising a sterile composition for injection, comprising (or consisting of): (a) about 58.3 mg/mL potassium monobasic phosphate; (b) about 100 mg/mL of potassium dibasic phosphate; and (c) a sufficient amount of a water vehicle; wherein the total amount of phosphate is about 1 mmol/mL, wherein the vial is comprised of glass or plastic. The vial may be sealed using suitable stoppers and flip-off tops, as described herein. The plastic vial optionally comprises a coating comprised of SiO2.

A third embodiment is directed to a sterile composition for injection, comprising: (a) about 136 mg/mL potassium monobasic phosphate and (b) a sufficient amount of a water vehicle; wherein the total amount of phosphate is about 1 mmol/mL.

A fourth embodiment is directed to a sterile composition for injection, consisting of: (a) about 136 mg/mL potassium monobasic phosphate and (b) a sufficient amount of a water vehicle; wherein the total amount of phosphate is about 1 mmol/mL.

In a first aspect of the third or fourth embodiment, the composition has an amount of potassium that is about 136 mg/mL.

In a second aspect of the third or fourth embodiment, the composition has a pH of about 4.0 to about 4.4.

In a third aspect of the third or fourth embodiment, the composition has a pH of about 4.1 to about 4.3.

In a fourth aspect of the third or fourth embodiment, the composition has a pH of about 4.2.

In a fifth aspect of the third or fourth embodiment, the composition has no visible particles after storage at 4-8° C. for 3-months, 6-months, 12-months, 18-months, 24-months, 30-months, 36-months, 42-months, 48-months, 54-months, 60-months, 66-months, 72-months, 78-months, 84-months, 90-months, or 96-months.

In a sixth aspect of the third or fourth embodiment, the composition has no visible particles after storage at about 25° C. for 3-months, 6-months, 12-months, 18-months, 24-months, or longer. The relative humidity of the storage may include ambient humidity or 60%.

A seventh aspect of the third or fourth embodiment is directed to a vial (e.g., glass or plastic) comprising the composition of the third or fourth embodiment. A particularly advantageous feature of the seventh aspect is that the composition has no visible particles after storage at 4-8° C. for 3-months, 6-months, 12-months, 18-months, 24-months, 30-months, 36-months, 42-months, 48-months, 54-months, 60-months, 66-months, 72-months, 78-months, 84-months, 90-months, or 96-months.

An eighth aspect of the third or fourth embodiment is directed to a glass vial comprising the composition of the third or fourth embodiment having an aluminum content of not more than about 5 ppm after storage at 4-8° C. for 3-months, 6-months, 12-months, 18-months, 24-months, 36-months, or longer (e.g., 72-months).

A ninth aspect of the third or fourth embodiment is directed to a glass vial comprising the composition of the third or fourth embodiment having an aluminum content of not more than about 5 ppm after storage at 25° C. for 3-months, 6-months, 12-months, 18-months, 24-months, 36-months, or longer (e.g., 60-months). The relative humidity of the storage may include ambient humidity or 60%. An aluminum content of not more than about after storage at 25° C. for 36-months or longer (e.g., 60-months) is particularly surprising when the composition is stored in a glass vial.

A tenth aspect of the third or fourth embodiment is directed to a plastic vial comprising the composition of the third or fourth embodiment having an aluminum content of not more than about 5 ppm, about 4 ppm, about 3 ppm, about 2 ppm, or about 1 ppm after storage at 4-8° C. for 3-months, 6-months, 12-months, 18-months, 24-months, 36-months, or longer (e.g., 72-months). The plastic vial optionally comprises a coating comprised of SiO2.

An eleventh aspect of the third or fourth embodiment is directed to a plastic vial comprising the composition of the third or fourth embodiment having an aluminum content of not more than about 5 ppm, about 4 ppm, about 3 ppm, about 2 ppm, or about 1 ppm after storage at room temperature for 3-months, 6-months, 12-months, 18-months, 24-months, 36-months, or longer (e.g., 72-months). The plastic vial optionally comprises a coating comprised of SiO2.

A twelfth aspect of the third or fourth embodiment is directed to a vial (e.g., glass or plastic) comprising the composition of the third or fourth embodiment, wherein a volume of the sterile composition is about 5 mL, about 7.5 mL about 15 mL, or about 50 mL.

A thirteenth aspect of the third or fourth embodiment is directed to a vial (e.g., glass or plastic) comprising the composition of the third or fourth embodiment, wherein a volume of the sterile composition is about 15 mL to about 16 mL.

A fourteenth aspect of the third or fourth embodiment is directed to a method for treating hypophosphatemia in a patient in need thereof, which comprises: diluting the composition of the third or fourth embodiment with a pharmaceutically acceptable diluent to obtain a diluted composition and intravenously administering the diluted composition to the patient.

A fifteenth aspect of the third or fourth embodiment is directed to a method for treating hypophosphatemia in a patient in need thereof, which comprises: diluting the composition of the third or fourth embodiment with a pharmaceutically acceptable diluent to obtain a diluted composition and intravenously administering the diluted composition to the patient, wherein the patient exposure to aluminum is less than about 10 mcg/kg/day, less than about 7.5 mcg/kg/day, or less than about 5 mcg/kg/day.

A sixteenth aspect of the third or fourth embodiment is directed to a method for treating hypophosphatemia in a patient in need thereof, which comprises: diluting the composition of the third or fourth embodiment with a pharmaceutically acceptable diluent to obtain a diluted composition and intravenously administering the diluted composition to the patient, wherein the patient exposure to aluminum is less than about 5 mcg/kg/day.

A seventeenth aspect of the third or fourth embodiment is directed to a process for preparing the composition of the third or fourth embodiment, which comprises: (a) dissolving an amount of potassium monobasic phosphate in a vessel containing a first amount of water that represents about 30% of the total amount of water; (b) adding a second amount of water that represents about 70% of the total amount of water to the composition of step (a); (c) filtering the composition of step (b) through a membrane having a plurality of pores each with a pore diameter of about 0.2 µm; (d) dispensing a volume of the composition of step (c) into a vial; (e) sealing the vial of step (d); (f) heating the vial of step (e) at a temperature of about 121° C. for about 15 minutes to about 30 minutes. Sealing the vials is accomplished using suitable stoppers and flip-off tops, as described herein.

The filter comprised of a membrane having a plurality of pores each with a pore diameter of about 0.2 µm comprises a membrane comprising a pharmaceutically acceptable polymer, for example, polyethersulfone or polyvinylidine difluoride.

An eighteenth aspect of the third or fourth embodiment is directed to a sterile composition for injection obtained by the process of the seventeenth aspect, which comprises: (a) about 136 mg/mL potassium monobasic phosphate and (b) a sufficient amount of a water vehicle; wherein the total amount of phosphate is about 1 mmol/mL.

A nineteenth aspect of the third or fourth embodiment is directed to a vial (e.g., glass or plastic) comprising the sterile composition for injection of the eighteenth aspect of the third or fourth embodiment, which comprises (or consists of): (a) about 136 mg/mL potassium monobasic phosphate and (b) a sufficient amount of a water vehicle; wherein the total amount of phosphate is about 1 mmol/mL, wherein a volume of the sterile composition is about 5 mL, about 7.5 mL about 15 mL, or about 50 mL.

A twentieth aspect of the third or fourth embodiment is directed to a glass vial comprising the sterile composition for injection of the eighteenth aspect of the third or fourth embodiment, which comprises (or consists of): (a) about 136 mg/mL potassium monobasic phosphate and (b) a sufficient amount of a water vehicle; wherein the total amount of phosphate is about 1 mmol/mL, wherein a volume of the sterile composition is about 5 mL, about 7.5 mL about 15 mL, or about 50 mL.

A twenty-first aspect of the third or fourth embodiment is directed to a plastic vial comprising the sterile composition for injection of the eighteenth aspect of the third or fourth embodiment, which comprises (or consists of): (a) about 136 mg/mL potassium monobasic phosphate and (b) a sufficient amount of a water vehicle; wherein the total amount of phosphate is about 1 mmol/mL, wherein a volume of the sterile composition is about 5 mL, about 7.5 mL about 15 mL, or about 50 mL. The plastic vial optionally comprises a coating comprised of SiO2.

Suitable vials, stoppers, and flip-off tops are as described herein.

It may be understood from the embodiments described herein that the "comprising" expression "comprising" may be replaced, where appropriate, by the "consisting of" expression.

EXAMPLES

As stated above, PPI products can exhibit visible particulates after storage. The visible particulates can arise from the glass, from precipitated potassium phosphate, or a combination of the two.

A judicious selection of the glass vial may serve to decrease particulates that arise from glass.

In an effort to understand the conditions under which precipitated potassium phosphate arises, studies were conducted on several compositions containing potassium phosphate.

Effect of pH and Temperature on Visible Particulates

Five test compositions (Test Compositions 1-5) containing 224 mg/mL of potassium monobasic phosphate (i.e., $KH_2PO_4$ or KMP), 236 mg/mL of potassium dibasic phosphate (i.e., K2HPO4 or KDP), water for injection (16 mL), and a pH adjuster ("pH Adj.") comprised of potassium hydroxide and/or hydrochloric acid to achieve a target pH ("$pH_t$") of 6.0 to 7.5 were prepared and stored in Fiolax clear glass vials (Schott AG, RC-DC) with grey B2-40 Westar RS stoppers.

A sixth test composition (Test Composition 6) containing 224 mg/mL of KMP, 236 mg/mL of KDP, water for injection (16 mL), with no pH adjuster was prepared and stored in Fiolax clear glass vials (Schott AG, RC-DC) with grey B2-40 Westar RS stoppers.

A seventh test composition (i.e., a PPI product) manufactured by Hospira (hereafter "Reference Product") was used for comparison.

The compositions were evaluated initially for Appearance (APP) and Visible Particles (VP) according to the Universal Test and USP 41 <790> Visible Particulates in Injections, as well as pH USP 41 <791>.

Although the package inserts for the marketed PPI products recommend storing either between 15° C. to 30° C. or between 20° C. to 25° C., it was recognized that in some instances products can be stored under a variety of conditions that deviate from the recommended storage conditions. Accordingly, the test compositions were evaluated after 12-weeks after storage under three conditions: (i) 2-8° C.; (ii) 25° C. and 60% relative humidity ("RH"), and (iii) 40° C. and 75% RH. The tested compositions conformed ("C") with no visible particulates, while the tested compositions did not conform ("NC") with visible particulates. Table 1 summarizes the results from these studies.

TABLE 1

Appearance and Visible Particulates in
Test Compositions 1-6 and Reference Product.

| Test Compositions | pH Adj. | $pH_t$ | $pH_0$ | Initial APP | Initial VP | 12-weeks 2-8° C. APP | 12-weeks 2-8° C. VP | 12-weeks 25° C./60% RH APP | 12-weeks 25° C./60% RH VP | 12-weeks 40° C./75% RH APP | 12-weeks 40° C./75% RH VP |
|---|---|---|---|---|---|---|---|---|---|---|---|
| TC 1 | Y | 6.0 | 6.1 | NC | >10 | NT | NT | NT | NT | NT | NT |
| TC 2 | Y | 6.5 | 6.5 | C | C | C | 1-5 | C | C | C | C |
| TC 3 | Y | 6.75 | 6.7 | C | C | C | 1-5 | C | C | C | C |
| TC 4 | Y | 7.0 | 7.0 | C | C | C | C | C | C | C | C |
| TC 5 | Y | 7.5 | 7.5 | C | C | C | C | C | C | C | C |
| TC 6 | N | — | 6.6 | C | C | NC | 1-5 | C | C | C | C |
| Ref. Prod. | N/A | — | 6.5 | C | C | NC | 1-5 | C | C | C | C |

The Table 1 results show that Test Compositions 1-5 included a pH adjuster, while Test Composition 6 and the Reference Product ("Ref. Prod.") did not. Table 1 reports the observed pH values ("pHo"), as well as the composition observations related to appearance ("APP") and visible particulates ("VP") initially and after twelve-weeks stored under the above-mentioned conditions of: (i) 2-8° C.; (ii) 25° C. and 60% RH, and (iii) 40° C. and 75% RH.

A test composition conforms ("C") to the appearance ("APP") test if the product is a clear and colorless solution. A product does not conform ("NC") to the appearance test if the test composition is not clear and colorless.

A test composition conforms to the visible particulate ("VP") test if the product contains no visible contaminants, while a non-conforming ("NC") product contains visible particulates.

As an initial matter, Test Composition 1 (TC 1) showed an extensive amount of precipitation during and after pH adjustment, and thus, TC 1 did not conform (NC). Accordingly, no further testing ("NT") of TC 1 occurred.

The test compositions stored for 12-weeks at either 25° C./60% RH or 40° C./75% RH conformed with respect to appearance and visible particulates. However, several of the test compositions failed to conform with respect to either appearance or visible particulates after storage for 12-weeks at 2-8° C. For instance, the test composition with no added pH adjuster (TC 6), as well as the Reference Product exhibited large colorless crystals after storage for 12-weeks at 2-8° C. Thus, it was concluded that these two test compositions did not conform. The results show that test compositions having a pH of either 6.5 (TC 2) or 6.7 (TC 3) failed to conform to the visible particulate test because of the appearance of 1-5 visible particulates.

It was determined that the average solubility of KMP at about 23° C. is 213±35 mg/mL. The average KMP solubility is consistent with a reported KMP solubility in about 4.5 parts water. See, e.g., Merck Index (1976), Monograph No. 7446 at 7447. The reported solubility of KMP in about 4.5 parts water corresponds to a solubility of about 222 mg KMP per mL, but the Merck Index does not state the temperature of the reported solubility of KMP in about 4.5 parts water. The reported solubility of about 222 mg KMP per mL is in general agreement with the reported solubility for KMP of 0.226 kg KMP per kg of water (or 226 mg/mL) at 20° C. See Mullin. As a point of reference, the marketed PPI products contain KMP at a concentration of 224 mg/mL. Thus, it can be seen that the amount of KMP in the marketed PPI product is close to the reported solubility limit for KMP when stored at about 20° C.

KDP is much more soluble in water, compared to KMP, with a KDP solubility of about 900 mg/mL. As a point of reference, the marketed PPI products contain KDP at a concentration of 236 mg/mL.

Based on the results from the above-mentioned experiments related to the test compositions coupled with the reported solubility values of KMP and KDP, it was believed that the concentration of KMP in the PPI products might be too high. It was hypothesized that the high concentration of KMP coupled with a failure to maintain control of storage conditions may contribute to the formation of visible particulates in marketed PPI products. In that regard, experiments were devised that evaluated potassium phosphate compositions having differing amounts of KMP and KDP.

Effect of KMP and KDP Concentration and Temperature on Visible Particulates

In an effort to understand the effect of KMP and KDP concentration and temperature on the formation of visible particulates, the inventors prepared additional compositions that varied the amount of KMP and KDP by 80% to 120% of the labeled content of PPI. As stated above, PPI contains 224 mg/mL of KMP and 236 mg/mL of KDP. Thus, 80% of the labeled content for KMP corresponds to 179.2 mg/mL KMP, while 120% of the labeled content for KDP corresponds to 283.3 mg/mL KDP. Further, 120% of the labeled content for KMP corresponds to 269.8 mg/mL KMP, while 80% of the labeled content for KDP corresponds to 188.8 mg/mL KDP. Table 2 summarizes the amounts of KMP and KDP in Test Compositions ("TC") 7-12.

TABLE 2

Makeup of Test Compositions 7-12 with varying Labeled Contents

| TC | KMP (mg/mL) | % L.C. KMP | KDP (mg/mL) | % L.C. KDP |
|---|---|---|---|---|
| 7 | 179.2 | 80 | 283.3 | 120 |
| 8 | 201.7 | 90 | 259.6 | 110 |
| 9 | 212.8 | 95 | 247.8 | 105 |
| 10 | 235.3 | 105 | 224.2 | 95 |
| 11 | 246.6 | 110 | 212.6 | 90 |
| 12 | 269.8 | 120 | 188.8 | 80 |

Initially, the test compositions were evaluated visually for the presence of a clear solution ("CS") or for the presence of a precipitate ("PPT"). The test compositions were subjected to a temperature of −15° C. until the compositions froze, and then the test compositions were allowed to thaw by storing the test compositions at room temperature. After thawing, the appearance of the undisturbed test compositions was evaluated. All test compositions showed some degree of precipitation ("PPT") that included a trace ("Tr.") amount of precipitation (TC 7), a light ("Lt.") amount of precipitation (TC 8), or a measurable amount of precipitation that varied from 2 mm to 15 mm (cf. TC 9-TC 12). Table 3 summarizes the observed appearances of Test Compositions 7-12.

TABLE 3

Observed Appearances of Test Compositions 7-12

| TC | Initial | −15° C.[a] | Before 5° C.[b] | After 5° C.[c] | 2 weeks at RT[d] |
|----|---------|------------|-----------------|----------------|------------------|
| 7  | CS      | PPT (Tr.)  | CS              | CS             | CS               |
| 8  | CS      | PPT (Lt.)  | CS              | CS             | CS               |
| 9  | CS      | PPT (2 mm) | CS              | CS             | CS               |
| 10 | CS      | PPT (10 mm)| PPT (Tr.)       | LCC            | LCC              |
| 11 | CS      | PPT (3 mm) | PPT (Tr.)       | LCC            | LCC              |
| 12 | PPT, Tr.| PPT (15 mm)| PPT (Tr.)       | LCC (2 mm)     | LCC (2 mm)       |

[a]Observation made after thawing without disturbing test composition.
[b]Observation made at room temperature after perturbation, but before cooling at 5° C.
[c]Observation made after composition reached room temperature.
[d]Room temperature ("RT") observations showed that some test compositions had a layer of clear crystals ("LCC") that did not return to solution after perturbation.

Once the test compositions reached room temperature, the test compositions were perturbed (i.e., mixing, shaking, and/or sonicating) to achieve a clear solution (CS). Table 3 summarizes these results in the column under the heading "Before 5° C." Clear solutions were observed for Test Compositions 7-9 having an amount of KMP that corresponds to 80-95% of labeled content. However, clear solutions were not observed for Test Compositions 10-12 having an amount of KMP that corresponds to 105-120% of labeled content.

The test compositions were then stored at a temperature of 5° C., removed from cold storage and, allowed to reach room temperature, and subsequently visually evaluated at room temperature. Table 3 summarizes these results in the column under the heading "After 5° C." The table shows that Test Compositions 7-9 existed as clear solutions, but that Test Compositions 10-12 contained a layer of clear crystals ("LCC") having a thickness of up to 2 mm. These crystals did not return to solution after perturbation.

From these results, it was concluded that test compositions having a KMP labeled content of from 105% to 120% formed insoluble particulate matter, especially when stored at sub-ambient temperatures. It also was concluded that although test compositions having a KMP labeled content from 80% to 95% formed particulate matter after freezing, this particulate matter could be dissolved after perturbation. However, Test Composition 7 showed the least amount of precipitation after freezing, and thus, identified as a composition for further consideration.

Example 1. Batch Preparation (700 g, 3 mmol Phosphates/mL)

A 700 gram batch using the same labeled content amounts as Test Composition 7 was prepared. Forty four percent of the required water (201.25 g) was added into a 1000 mL beaker. Upon addition of the requisite amount of KDP (to provide a final concentration of 283.3 mg/mL), the mixture was stirred until the KDP dissolved. Dissolution of KDP is an exothermic process, and the recorded temperature after dissolution was 32° C. The recorded pH was 10.37.

The requisite amount of KMP (to provide a final concentration of 179.2 mg/mL) was then added to the KDP-containing solution. The KMP did not dissolve completely. Accordingly, an additional 107.25 grams of water (totaling 308.5 g or 68% of required water) was added to the solution. After mixing, the composition contained undissolved KMP. An additional 50 grams of water was added and the remaining amount of KMP dissolved. Total water at this point was approximately 79% of the required water (total required water is 453.96 grams). The pH was recorded at 7.65. Temperature was 23° C. The remaining water was added (total amount added was 453.96 grams) and the final pH was 7.55.

The produced batch had a KMP concentration of 179.2 mg/mL. The difficulty observed in dissolving the KMP during batch preparation is consistent with the above-mentioned solubility experiments. Accordingly, a subsequent batch was contemplated where the KMP was not added until about 79% of the total amount of water had been added.

Based on the observations gleaned from preparation of the above-mentioned batch, it was determined that a solution containing about 175 g KMP, about 300 g KDP, and water (q.s. 1-L) would provide a robust formulation ensuring solubility of KMP, and thus, preventing the formation of undesirable visible particulates. The specified amount of KMP and KDP results in the same millimolar quantity of phosphate (i.e., 3 mmol phosphate/mL) as the marketed PPI products. With the differing amounts of KMP and KDP, the amount of potassium increases from 4.4 mEq/mL to 4.7 mEq/mL (i.e., about 185 mg potassium/mL).

Example 2. Batch Preparation (200 L Batch, 3 mmol Phosphates/mL)

A 200 L batch was manufactured having the composition described in the following table.

| Ingredient | Quantity (g) |
|------------|--------------|
| Potassium Phosphate Monobasic NF | 35,000.000 |
| Potassium Phosphate Dibasic USP  | 60,000.000 |
| Water for injection              | 265,740.000[a] |

[a]Density of Solution: 1.3287 g/mL

Approximately 25% of the total amount of water for injection (WFI) was added to a suitable compounding vessel equipped with a stirring mechanism. Sixty kg of KDP was added to said vessel and the liquid was stirred at a rate of 300-450 rpm for at least about 30-minutes until all KDP had dissolved. The solution at this point was clear and colorless with no visible particulate matter. Approximately 60% of the total amount of the WFI was added to the compounding vessel and was stirred at a rate of 300-450 rpm for at least about 30-minutes. Thereafter, 35 kg of KMP was added to said vessel and the liquid was stirred at a rate of 300-450 rpm until all KMP had dissolved. The solution was clear and colorless with no visible particulate matter. The remaining 15% of WFI was added to the vessel and the solution was stirred at a rate of 300-450 rpm for at least about 30-minutes. After stirring, the recorded pH-value was about 6.9 with a process specification of about 6.8 to about 7. The vessel was sparged with nitrogen.

The composition held in the compounding vessel was filtered into a storage vessel using a membrane having a plurality of pores each with a pore diameter of about 0.2 μm. The head space of the storage vessel was sparged with nitrogen (overpressure of about 0.5 bar 7.3 psi)) and the composition was passed through a membrane having a plurality of pores each with a pore diameter of about 0.2 µm, while metering a desired volume into a vial (e.g., VIA INJEKT 20 R DC clear EBB TYP1 Schott). The vial was then fitted with a rubber stopper (e.g., STV 1242 4110/40/ grey B2-40 WESTAR RS) and a flip-off cap (e.g., VS FLIP-OFF grey 20MM SFC 20.0001) and subsequently crimped.

Another vial configuration includes a plastic vial manufactured by SiO2 Medical, including, for example, a medical grade cyclic olefin polymer (COP) with (e.g., SiO2Plas Vial (COP with SiO2 coating) 2R, 6R, 10R, or 20R) or without a SiO2 coating (e.g., COP Vial 2R, 6R, 10R, or 20R). The vials were then fitted with a suitable stopper manufactured by, for example, West Pharmaceuticals, and include 20 mm Serum NovaPure RP S10-F451 4432/50G (gray elastomer having FluroTec® barrier film) fitted with a suitable flip-off top manufactured by, for example, Datwyler Pharma Packaging, 20F0 LQ TE (6-B) 3766 WHT (aluminum closure with white Flip top cap).

Development studies showed that filtration using a filter membrane comprised of polyvinylidine difluoride may not adequately sterilize the composition comprised of about 175 mg/mL potassium monobasic phosphate; about 300 mg/mL of potassium dibasic phosphate; and a sufficient amount of a water vehicle, as evidenced by testing related to *B. diminuta*. However, a filter membrane comprised of a polyethersulfone was shown to adequately sterilize the above-mentioned composition.

Some vials (aseptic samples) were set aside for further analysis, while other vials were terminally sterilized (TS samples). Each vial contains about 175 mg/mL KMP, about 300 mg/mL KDP, and (c) a sufficient amount of a water vehicle to provide total amount of phosphate of about 3 mmol/mL.

The vials were assayed over time for appearance, visual particulate matter, potassium, KMP, and KDP, according to the respective USP assays. The aluminum content was assayed using ICD-OES (i.e., inductively coupled plasma/ optical emission spectroscopy) as measured by an Agilent 725 ICP-OES.

Importantly, none of the vials demonstrated any visible particulate matter at the time of manufacture and after storage for 18-months at 4-8° C., 25° C./60% RH, and 40° C./75% RH. The observation of no visible particulate matter after storage for 18-months at 4-8° C. is particularly surprising because the estimated solubility of KMP at 4-8° C. is about 135 mg/mL to about 157 mg/mL. See Mullin. It is estimated that the composition shows no visible particulates after storage at 4-8° C. for 24-months or longer (up to, for example, 96-months). Storing the vials at 4-8° C. is of particular importance for reducing the amount of aluminum in glass vials.

The initial aluminum assays for the aseptic glass vials (2.4 ppm) and terminal sterilized glass vials (5.8 ppm) shows that terminal sterilization is a source of aluminum in the composition. Additionally, aluminum continues to leach from the glass into the composition after storage for an extended period. The following table summarizes the aluminum content for terminal sterilized glass vials stored at either 4-8° C. or 25° C./60% RH, initially (0M), at 3-months (3M), at 12-months (12M), and at 18-months (18M).

| Storage Conditions | Aluminum Content, ppm | | | |
| --- | --- | --- | --- | --- |
| | 0M | 3M | 12M | 18M |
| 4-8° C. | 5.8 | 5.2 | 6.3 | 6.2 |
| 25° C./60% RH | 5.8 | 8.2 | 14.3 | 16.8 |

An aluminum assay using ICP-OES shows that the aluminum content of the compositions of the terminally stabilized glass vials is about 16.8 ppm when the glass vial is stored for 18-months at 25° C./60% RH. The 16.8 ppm assay amount should be contrasted to the glass vials stored for 18-months at 4-8° C., where the aluminum content is reduced by a factor of about 2.7 to 6.2 ppm.

Based on these and other results, it is estimated that the composition of the first or second embodiment has an aluminum content of not more than about 10 ppm after storage at 4-8° C. for 18-months or longer (up to, for example, 24-months). Further, it is estimated that the composition of the first or second embodiment has an aluminum content of not more than about 15 ppm after storage at 4-8° C. for 36-months or longer (up to, for example, 48-months).

The reduction in aluminum content with storage at 4-8° C. is particularly advantageous because it provides for a composition of the first or second embodiment that can be administered to patients with renal insufficiency that does not exceed the recommended maximum daily aluminum dose of 4 to 5 mcg/kg/day. See Poole (2011).

Tests conducted in a plastic vial (e.g., with a medical grade cyclic olefin polymer (COP) with or without a SiO2 coating) on a composition of the first or second embodiment shows an aluminum content of not more than about 5 ppm (viz., about 0.2 to about 0.3 ppm) after storage at 60° C. at 60% relative humidity for 0.5- and 1.0-months. Based on these results, it is contemplated that a composition of the first or second embodiment stored in a plastic vial may be stored at room temperature.

Example 3. Batch Preparation (1 L, 1 mmol KMP/mL)

A 1 L batch was manufactured having the composition described in the following table.

| Ingredient | Quantity (g) |
| --- | --- |
| Potassium Phosphate Monobasic NF | 136.000 |
| Water for injection | 1,088.000[a] |

[a]Density of Solution: 1.088 g/mL

Approximately 30% of the total amount of WFI was added to a suitable compounding vessel equipped with a stirring mechanism. 136.000 g of KMP was added to said vessel and the liquid was stirred at a rate of 300-450 rpm for at least about 30-minutes until all KMP had dissolved. The solution at this point was clear and colorless with no visible particulate matter. Approximately 70% of the total amount of the WFI was added to the compounding vessel and was stirred at a rate of 300-450 rpm for at least about 30-minutes. The solution was clear and colorless with no visible particulate matter. After stirring, the recorded pH-value was about 4.2. The vessel may be sparged with nitrogen.

The composition held in the compounding vessel may be filtered into a storage vessel using a membrane having a plurality of pores each with a pore diameter of about 0.2 The head space of the storage vessel may be sparged with nitrogen (overpressure of about 0.5 bar 7.3 psi)) and the composition may be passed through a membrane having a plurality of pores each with a pore diameter of about 0.2 µm, while metering a desired volume into a vial (e.g., VIA INJEKT 20 R DC clear EBB TYP1 Schott). The vial then may be fitted with a rubber stopper (e.g., 20 mm Serum NovaPure RP S10-F451 4432/50G (gray elastomer having FluroTec® barrier film) and a flip-off cap (e.g., 20F0 LQ TE (6-B) 3766 WHT (aluminum closure with white Flip top cap) and subsequently crimped. Additional vial configurations are as described herein.

The aluminum content of terminally sterilized (autoclave, 121° C. (about 30-minutes)) glass vials containing about 15 mL each of the Example 3 composition was analyzed using ICP-OES after storage at a set temperature (e.g., 5° C., 25° C., 40° C., and 60° C.) and ambient humidity. The aluminum content values initially (0M), 1-month (1M), 2-months (2M), and 3-months (3M) are as shown below.

| Storage Conditions | Aluminum Content, ppm | | | |
| --- | --- | --- | --- | --- |
| | 0M | 1M | 2M | 3M |
| 4-8° C. | 0.70 | 0.69 | 0.82 | 0.82 |
| 25° C. | 0.70 | 0.39 | 0.77 | 1.56 |
| 40° C. | 0.70 | 1.02 | 1.48 | 1.86 |
| 60° C. | 0.70 | 2.39 | 4.42 | 5.34 |

The observed aluminum content vales after three-months at the given temperatures are: 0.82 ppm (5° C.), 1.56 ppm (25° C.), 1.86 ppm (40° C.), and 5.34 ppm (60° C.). Based on these results, it is contemplated that a composition of the third or fourth embodiment stored in a glass vial may be stored at 25° C.

The present application claims priority to U.S. Provisional Patent Application No. 62/748,008, filed on Oct. 19, 2018 ("the related application"), the subject matter of which is incorporated by reference in its entirety.

Alternative embodiments, examples, and modifications which would still be encompassed by the disclosure may be made by those skilled in the art, particularly in light of the foregoing teachings. Further, it should be understood that the terminology used to describe the disclosure is intended to be in the nature of words of description rather than of limitation.

CITED REFERENCES

*Aluminum in Large and Small Volume Parenterals Used in Total Parenteral Nutrition*, Federal Register, Jan. 26, 2000, Vol. 65, No. 17, 4103-4111 ("FDA Regulations (2000)").

Mullin et al., *Growth Kinetics of Ammonium- and Potassium-Dihydrogen Phosphate Crystals*, J. Appl. Chem. (1967) 17(5): 151-156 ("Mullin").

Poole et al., *Aluminum in Pediatric Parenteral Nutrition Products: Measured Versus Labeled Content*, J. Pediatr. Pharmacol. Ther. (2011) 16(2): 92-97 ("Poole (2011)").

Poole et al., *Aluminum Exposure from Pediatric Parenteral Nutrition: Meeting the New FDA Regulation*, J. Parenter. Enteral. Nutr. (2008) 32(3): 242-246 ("Poole (2008)").

Ogawa et al., *Effects of Phosphate Buffer in Parenteral Drugs on Particle Formation from Glass Vials*, Chem. Pharm. Bull. (2013) 61(5): 539-545 ("Ogawa (2013)").

Ogawa et al., *Aluminum elution and precipitation in glass vials: effect of pH and buffer species*, Drug Dev. Ind. Pharm. (2015) 41(2): 315-321 ("Ogawa (2015)").

The Merck Index, Ninth Edition (1976) ("Merck Index (1976)").

U.S. Patent Application Publication No. 2015/0297800 A1, SiOx Barrier for Pharmaceutical Package and Coating Process, published on Oct. 22, 2015 to Weikart et al. ("Weikart (2015)").

U.S. Patent Application Publication No. 2018/0221243 A1, Trilayer coated Blood Collection Tube with Low Oxygen Transmission Rate, published on Aug. 9, 2018 to Weikart et al. ("Weikart (2018)").

The references described herein are incorporated by reference in their entirety to the extent necessary. In the event that there is a difference in meaning between the incorporated terms and the terms disclosed herein and the terms of the related application, the meaning of the terms disclosed herein and the related application will control.

Those skilled in the art will also appreciate that various adaptations and modifications of the preferred and alternative embodiments described above can be configured without departing from the scope and spirit of the disclosure. Therefore, it is to be understood that, within the scope of the appended claims, the disclosure may be practiced other than as specifically described herein.

The invention claimed is:

1. A sterile composition for injection, consisting of:
   (a) 175 mg/mL potassium monobasic phosphate;
   (b) 300 mg/mL of potassium dibasic phosphate; and
   (c) a sufficient amount of a sterile water vehicle;
   wherein the sterile composition has a total amount of phosphate content of 3 mmol/mL, a potassium content of 185 mg/mL, and an aluminum content of not more than 15 ppm;
   wherein the sterile composition for injection has no visible particles after (i) storage at 4-8° C. for 24-months or (ii) storage at 25° C. and 60% relative humidity for 24-months;
   wherein the composition is contained in a vial; and
   wherein the vial is comprised of glass or plastic.

2. The composition of claim 1, wherein the sterile composition for injection has a pH of about from 6.5 to about 7.5.

3. The composition of claim 1, wherein the sterile composition for injection has a pH of about from 6.8 to about 7.0.

4. The composition of claim 1, wherein the vial is comprised of glass and wherein the sterile composition for injection has an aluminum content of not more than 15 ppm after storage at 4-8° C. for 24-months.

5. The composition of claim 1, wherein the vial is comprised of plastic and wherein the sterile composition for injection has an aluminum content of not more than 5 ppm after storage for 48-months either at 4-8° C. or at 25° C. and 60% relative humidity.

6. The composition of claim 1, wherein a volume of the sterile composition for injection is 5 mL, 7.5 mL, 15 mL, or 50 mL.

7. The composition of claim 1, wherein a volume of the sterile composition for injection ranges from 15 mL to 16 mL.

8. A sterile composition for injection, consisting of:
   (a) 175 mg/mL potassium monobasic phosphate;
   (b) 300 mg/mL of potassium dibasic phosphate; and
   (c) a sufficient amount of a sterile water vehicle;
   wherein the sterile composition for injection has a phosphate content of 3 mmol/mL, a potassium content of 185 mg/mL, and an aluminum content of not more than 15 ppm; wherein the composition is contained in a glass vial; and wherein the sterile composition for injection has no visible particles after (i) storage at 4-8° C. for 24-months or (ii) storage at 25° C. and 60% relative humidity for 24-months.

9. The composition claim 8, wherein the sterile composition for injection has a pH that ranges from 6.8 to 7.0.

10. The composition of claim 8, wherein a volume of the sterile composition for injection is 5 mL, 7.5 mL, 15 mL, or 50 mL.

11. The composition of claim 8, wherein a volume of the sterile composition for injection ranges from 15 mL to 16 mL.

12. A sterile composition for injection, consisting of: a potassium phosphate solution in a sterile water vehicle;

wherein the sterile composition for injection has: (i) a pH of from 6.5 to 7.5, (ii) a phosphate content of 3 mmol/mL, (iii) a potassium content of 4.7 mEq/mL, and (iv) an aluminum content of not more than 15 ppm;

wherein the sterile composition for injection has no visible particles after (a) storage at 4-8° C. for 24-months or (b) storage at 25° C. and 60% relative humidity for 24-months; wherein the composition is contained in a vial; and wherein the vial is comprised of glass or plastic.

13. The composition of claim 12, wherein the sterile composition has a pH of from 6.8 to 7.0.

14. The composition of claim 12, wherein a volume of the sterile composition is 5 mL, 7.5 mL, 15 mL, or 50 mL.

15. The composition of claim 12, wherein the vial is comprised of glass and wherein the sterile composition for injection has an aluminum content of not more than 15 ppm after storage at 4-8° C. for 24-months.

16. The composition of claim 12, wherein the vial is comprised of plastic and wherein the sterile composition for injection has an aluminum content of not more than 5 ppm after storage for 48-months either at 4-8° C. or at 25° C. and 60% relative humidity.

17. The composition of claim 12, wherein a volume of the sterile composition ranges from 15 mL to 16 mL.

18. A method for treating hypophosphatemia in a patient in need thereof, which comprises:
(a) diluting the sterile composition for injection of claim 7 with a pharmaceutically acceptable diluent to obtain a diluted composition and
(b) intravenously administering the diluted composition to the patient;
wherein the patient exposure to aluminum is less than 5 mcg/kg/day.

19. A process for preparing the composition of claim 1, which comprises:
(a) dissolving an amount of potassium dibasic phosphate in a vessel containing a first amount of sterile water that represents 25% of the total amount of water;
(b) adding a second amount of sterile water that represents 60% of the total amount of water to the composition of step (a);
(c) dissolving an amount of potassium monobasic phosphate in the composition of step (b);
(d) adding a third amount of water to the composition of step (c); and
(e) filtering the composition of step (d) through a membrane having a plurality of pores each with a pore diameter of 0.2 μm;
(f) dispensing a volume of the composition of step (e) into a vial;
(g) sealing the vial of step (f); and
(h) heating the vial of step (g) at a temperature of 121° C. for 15 to 30 minutes.

20. A method for treating hypophosphatemia in a patient in need thereof, which comprises:
(a) diluting the sterile composition for injection of claim 11 with a pharmaceutically acceptable diluent to obtain a diluted composition and
(b) intravenously administering the diluted composition to the patient;
wherein the patient exposure to aluminum is less than 5 mcg/kg/day.

21. A method for treating hypophosphatemia in a patient in need thereof, which comprises:
(a) diluting the sterile composition for injection of claim 17 with a pharmaceutically acceptable diluent to obtain a diluted composition and
(b) intravenously administering the diluted composition to the patient;
wherein the patient exposure to aluminum is less than 5 mcg/kg/day.

* * * * *